(12) United States Patent
Gemon et al.

(10) Patent No.: US 11,653,977 B2
(45) Date of Patent: May 23, 2023

(54) ANCILLARY DEVICE AND METHOD FOR DETERMINING AN ANCILLARY DEVICE

(71) Applicant: 3D MEDICAL, Marolles-en-Brie (FR)

(72) Inventors: Jean-Pierre Gemon, Bordeaux (FR); Vincent Nuttens, Brunoy (FR)

(73) Assignee: 3D MEDICAL, Marolles-en-Brie (FR)

( * ) Notice: Subject to any disclaimer, the term of this patent is extended or adjusted under 35 U.S.C. 154(b) by 249 days.

(21) Appl. No.: 16/480,256

(22) PCT Filed: Jan. 23, 2018

(86) PCT No.: PCT/FR2018/050152
§ 371 (c)(1),
(2) Date: Jul. 23, 2019

(87) PCT Pub. No.: WO2018/134545
PCT Pub. Date: Jul. 26, 2018

(65) Prior Publication Data
US 2019/0380783 A1 Dec. 19, 2019

(30) Foreign Application Priority Data
Jan. 23, 2017 (FR) .................... 17 50543

(51) Int. Cl.
*A61B 17/17* (2006.01)
*A61B 34/10* (2016.01)
*A61B 90/00* (2016.01)
*A61B 17/15* (2006.01)

(52) U.S. Cl.
CPC ............ *A61B 34/10* (2016.02); *A61B 17/175* (2013.01); *A61B 17/1757* (2013.01); *A61B 17/1764* (2013.01); *A61B 17/1778* (2016.11); *A61B 17/154* (2013.01); *A61B 2034/108* (2016.02); *A61B 2090/374* (2016.02); *A61B 2090/3762* (2016.02)

(58) Field of Classification Search
CPC .................................................. A61B 17/1764
See application file for complete search history.

(56) References Cited

U.S. PATENT DOCUMENTS

| 2012/0277751 | A1* | 11/2012 | Catanzarite | .......... | A61B 17/155 |
| | | | | | 606/88 |
| 2015/0051602 | A1* | 2/2015 | Uthgenannt | ......... | A61B 17/157 |
| | | | | | 606/88 |
| 2018/0235641 | A1* | 8/2018 | McAuliffe | ........... | A61B 17/157 |

FOREIGN PATENT DOCUMENTS

| FR | 2938178 A1 | 5/2010 |
| FR | 3024027 A1 | 1/2016 |
| WO | WO 2016/074733 A1 | 5/2016 |

OTHER PUBLICATIONS

International Search Report related to Application No. PCT/FR2018/050152; dated April 4. 2018.

* cited by examiner

*Primary Examiner* — Olivia C Chang
(74) *Attorney, Agent, or Firm* — von Briesen & Roper, s.c.

(57) ABSTRACT

The invention relates to a guiding ancillary device designed to cooperate with at least two bone surfaces, and to the method for the production thereof. The invention also relates to a guiding ancillary device for use in orthopedic surgery, and to an assembly comprising a guiding ancillary device and at least one medical device.

16 Claims, 3 Drawing Sheets

ANCILLARY DEVICE AND METHOD FOR DETERMINING AN ANCILLARY DEVICE

CROSS-REFERENCE TO RELATED APPLICATION

This Application is a 35 USC § 371 US National Stage filing of International Application No. PCT/FR2018/050152 filed on Jan. 23, 2018 and claims priority under the Paris Convention to French Patent Application No. 17 50543 filed on Jan. 23, 2017.

FIELD OF THE DISCLOSURE

The present invention relates to the field of orthopedic surgery and more particularly to a guiding ancillary device and its method of manufacture. The present invention also relates to a guiding ancillary device for its use in surgery.

BACKGROUND OF THE DISCLOSURE

Orthopedic surgery treats diseases, trauma (fractures, tears, hematomas) and deformations of the locomotor system: bones, joints, ligaments, tendons and muscles. Once limited to the treatment of fractures alone, it has since developed into other areas: prosthetic joints or endoscopic surgery.

This area has undergone numerous technological advances due to the large amount of instrumentation necessary for its implementation, particularly as regards ancillary devices, defined as instruments intended to guide the tools necessary for the surgical procedure.

The development of communication technologies, computing tools and robots has grown enormously, especially in orthopedic surgery. The difficulty lies in reproducing, in a three-dimensional environment, a plan that has been devised in two dimensions. Robotic surgery has thus been introduced and is presented as a tool whose maneuvers are performed wholly or partly by robot. The constraints associated with the use of active or semi-active robots in the operating theater may be linked to the reluctance on the part of surgeons to leave a surgical maneuver to a machine, but also to high investment costs and considerable maintenance issues.

A passive system has been developed more widely in recent years. Navigation involves a system of spatial orientation in relation to the anatomy of the patient. This navigation system corresponds to a measurement tool whose values are retranscribed in a central unit with an interface for the surgeon. Navigation allows increased accuracy and reproducibility of surgery. Preoperatively, it is possible to plan the intervention in the computer of the navigation system with images loaded onto the computer. The interface shows a representation of the anatomy of the operating site with the possibility of combining the loaded imaging plates, graphics or measurements performed in real time and with high precision. During the intervention, it permits representation of the anatomical parts that are not visible and allows real-time monitoring of the instruments or the alignment of the implants.

Navigation has permitted improved precision in the implantation of prostheses and in other orthopedic areas (scoliosis surgery, corrective osteotomy, traumatology). However, the operating time is extended by the use of navigation. The size of the operating theater is also considerable. Finally, the initial investment cost and maintenance costs are not inconsiderable for small and medium-sized organizations.

Despite the improved precision achieved by means of robots and remote navigation, the increased amount of instrumentation and the increased number of surgical steps, responsible for an increase in the duration of the procedure, do not favor economic profitability.

Customized guides appeared in the mid 1990s. From volumetric preoperative imaging, specific software defines reference points for positioning on the patient a customized guide that will allow plans to be recorded on the computer without changes or adjustments during the intervention.

Initially a plastic block was cut to size in order to follow the exact bone reliefs of the patient modeled in 3D. Such blocks can be used as an interface between the bone and the standard ancillary device or as a guide for positioning a drill bit, a pin or a saw.

Thereafter, the technology really took off thanks to technical improvements in rapid prototyping, permitting rapid 3D printing with increased precision, greater variety of available materials and lower costs.

In 2006, Hafez et al. described the modern procedure for performing surgery with customized instrumentation for total knee replacement:

Computed tomography (CT) or magnetic resonance imaging (MRI) of the lower limb is performed, targeting the knee, hip and ankle.

Data is transferred securely to a specialized center for 3D reconstruction after segmentation of the sections.

Preoperative 3D planning (size of the implants, positioning of the implants, necessary bone cuts, bone landmarks for placement of the guide) is performed by an engineer, with superpositioning of the implants on the bone, and alignment of the lower limb as reference.

Final control returns to the surgeon, who can modify all the parameterized data on the alignment and positioning of the implants. He validates the planning and the markers adapted to the surgical approach for positioning the guide.

The cutting guide is manufactured using a rapid prototyping process.

Customized guides have thus been developed in orthopedics to improve the precision of the bone cuts and to reduce the time associated with this procedure. They allow the surgeon, during the intervention, to apply planning that has been carried out on 3D reconstructed images. It is in knee surgery, particularly in total knee arthroplasty, that they have been developed most. There are other applications for the knee, hip, shoulder or ankle primarily in the context of arthroplasty but also, as regards the spine, for positioning the pedicle screws in the context of tumor resections for guiding the bone cuts without penetrating the lesion, and for corrective osteotomy of limbs.

The guides are provided for the positioning of pins or for directing cuts. The pin-positioning guides allow introduction of the pins that will guide the positioning of the standard cutting guide. The withdrawal of the customized guide for arranging the standard cutting guide increases the risk of imprecision linked to the weakness of the bone and to the modification of the position of the pins during the maneuver.

Cutting guides are the ones most represented among manufacturers, positioned on the bone by virtue of the specific bone markers fixed by two or three pins in order to increase their stability, they are provided with a slot through which the saw serving to cut the bone passes exactly. The femoral guide is fixed to the distal part of the femur, it allows the distal cut to be made and permits the marking of references for the positioning of the so-called "4 in 1" guide, permitting production of the anterior cuts, the posterior cuts, and also the anterior and posterior bevels. The tibial guide is fixed to the anterior and proximal part of the tibia, it allows the proximal cut of the tibia ( ).

Finally, the ancillary devices for cutting by sawing known from the prior art are studied and designed to implant standard prostheses.

The surgical technique of implanting a total knee prosthesis is an invasive technique and causes trauma to the anatomical structure. The access routes to the knee joint require the dislocation of the joint. Moreover, it may be necessary to sacrifice the anterior cruciate ligament and/or posterior cruciate ligament.

Moreover, customized cutting guides are designed to adapt to each bone surface in order to perform cutting of the bone, which may cause an offset and imbalance of the joint during the bone cutting.

There is therefore a need for an ancillary device able to cooperate with several bone surfaces, allowing better stability and better anchoring of the ancillary device. There is also a need for an ancillary device that does not require dislocation of the joints or the sacrifice of ligaments attached thereto and that preserves the anatomical structures. Finally, there is a need for a tailor-made ancillary device that permits implantation of a tailor-made prosthesis.

SUMMARY OF THE DISCLOSURE

The present invention aims to overcome the disadvantages of the prior art and to meet the constraints set out above by proposing a guiding ancillary device intended to cooperate with at least two bone surfaces.

The present invention also relates to a method for manufacturing a guiding ancillary device.

It also relates to a guiding ancillary device for its use in orthopedic surgery.

It moreover relates to an assembly comprising a guiding ancillary device according to the present invention and at least one medical device.

The invention thus relates to a guiding ancillary device intended to cooperate with at least two bone surfaces, characterized in that it comprises:
for each bone surface, a bearing surface intended to match at least partially a portion of the corresponding bone surface; said bearing surface additionally delimits at least one working zone on said bone surface when it is in contact with said bone surface;
said bearing surfaces being configured for maintaining said ancillary device in position on the corresponding bone surfaces, and
at least one guide means adapted to receive at least one medical device, said at least one guide means guiding the medical device to said working zone on the corresponding bone surface.

The term bone surface within the context of the invention is understood as the end of a bone or the outer surface of part of a bone.

The term bearing surface within the context of the invention is understood as the part of the ancillary device intended to come into contact with at least part of the corresponding bone surface.

The guiding ancillary device within the context of the present invention is defined and realized in particular after acquisition of one or more images by computed tomography (CT scan) and/or magnetic resonance imaging (MRI) or any other method of acquisition of images of at least two bone surfaces and 3D representation of the images thus obtained, and determination of the modifications to be made to at least one of the bone surfaces. Thus, the ancillary device, through each of its bearing surfaces, at least partly matches a portion of the corresponding bone surface and thus permits precise referencing of the surface of at least part of the bone surface. The ancillary device will be determined by in particular and at least the determination of at least one modification to be made to at least one of the bone surfaces. Thus, in contrast to a customized ancillary device permitting placement of a standard implant, the ancillary device according to the present invention is a tailor-made ancillary device adapting not only to the characteristics such as the shape, dimensions, bone surfaces with which it is intended to be used, but especially to the modifications and/or interventions to be made to at least one of the bone surfaces of each patient. This tailor-made ancillary device is thus adapted and customized for each intervention on each patient and thus cannot be reusable.

Advantageously, the bearing surfaces of the ancillary device make it possible to maintain and secure it in position and thus reduce the risk of its displacement. The ancillary device according to the present invention thus permits better alignment of said ancillary device with at least two bone surfaces during the surgical procedure. In addition to this function of improved bearing, each bearing surface of said guiding ancillary device makes it possible to define a working zone.

Within the context of the present invention, a working zone is understood as the zone of the bone surface delimited by the bearing surface of the guiding ancillary device according to the present invention.

The bearing surfaces of the guiding ancillary device each delimit a working surface, and the guide means will direct the medical devices to the working zone of each of the corresponding bone surfaces.

A medical device within the context of the present invention is understood as any instrument, apparatus, appliance, material used alone or in combination for use in the diagnosis, prevention and/or treatment of disease, the study, the replacement or modification of the anatomy or of a physiological process. Purely by way of illustration, these may include a sighting instrument, a milling instrument, a drilling instrument, a vertebroplasty instrument, a screwing instrument, a cell destruction instrument, a cell excitation instrument, a biopsy instrument, a sawing instrument, a probe, a catheter, a balloon, a stent, and any instrument taking reference to the bone for an intervention or measurement or positioning.

Within the context of the present invention, a guide means is understood as any means for guiding the movement of a medical device to at least one predefined working zone. For example, these may be a tubular member, oriented slits, a displacement path, or combinations of these features.

In addition, the guiding ancillary device within the context of the present invention allows the ancillary device to be positioned on at least two bone surfaces in order to guide at least one medical device. The anatomical structures are thus advantageously preserved. Advantageously, this ancillary device does not therefore involve dislocation of the joint during its implantation, nor any sacrifice of ligaments.

In various particular embodiments of the guiding ancillary device, each having its specific advantages and being open to numerous possible technical combinations:

The guiding ancillary device is in one piece.

The guiding ancillary device, being in one piece according to the present invention, thus permits intimate and stable contact with at least two bone surfaces, thus imposing a unique orientation and affording maximum stability of the ancillary device according to the present invention.

The guiding ancillary device has at least two ancillary parts, each of the ancillary parts being intended to cooperate with at least one distinct bone surface.

Typically, and in this embodiment, the ancillary device comprises at least one connection means for joining said at least two ancillary parts together.

Typically, the connection means or joining means is rigid or not rigid.

Each ancillary part has a female connection portion and/or a male connection portion, two ancillary parts intended to be immediately contiguous when said ancillary device is assembled, having a female connection zone and a male connection zone that are intended to cooperate with each other to allow said two ancillary parts to be joined together, at least some of said ancillary parts comprising at least one guide means, said guide means being separate, or at least some of said ancillary parts comprising a guide means portion, said guide means portions being separate and intended to form a guide means when said ancillary parts are joined to each other.

Purely by way of illustration, and in the case where the ancillary device is composed of two ancillary parts, a first ancillary part has, at its end opposite to the one intended to bear on the corresponding bone surface, a male connection portion, which is intended to cooperate with a female connection portion placed at a corresponding end of the second ancillary part so as to ensure stable assembly of said first and second ancillary parts. Of course, these connection portions advantageously permit their separation after connection, such that the latter can be temporary. The connection may thus be effected by snap-fastening, by interlocking, etc.

Purely by way of illustration, the connection means is chosen from among a hinge, a joint, a guide means permitting a translation movement or a rotation movement.

The connection means will be able to be a reference surface permitting movement by sliding, an abutment.

Typically, the reference surface permitting the sliding movement will be chosen from among a rail or a path of movement. Said ancillary parts comprise, for each male or female connection zone, at least one error-proofing means to prevent the connection of ancillary parts that are not intended to be immediately adjacent when the ancillary device is assembled.

The ancillary parts are configured to define at least two axes for guiding one or more different medical devices when they are connected to each other.

In a preferred embodiment, the ancillary parts are configured to define four or five axes for guiding one or more different medical devices when they are connected to each other.

Each ancillary part comprises, for each bone surface, a bearing surface intended to match at least partially a portion of said corresponding bone surface, said bearing surface delimiting a working zone on said bone surface, each part comprising at least two guide means, said at least two guide means defining distinct working axes for guiding the movement of at least one medical device along said working axes on the corresponding bone surface.

The guiding ancillary device is configured to cooperate with two bone surfaces.

Preferably, the two bone surfaces are the bone surface of the tibia and the bone surface of the femur, preferably the bone surface of the proximal end of the tibia and the bone surface of the distal end of the femur.

More preferably, each bearing surface is an impression of the portion of the bone surface of the distal end of the femur and the proximal end of the tibia femur, when the knee is in the anatomical reference position, and does not follow the bone surfaces of the intra-articular cavity.

Thus, very advantageously, when the ancillary device according to the present invention is configured to cooperate with two bone surfaces, for example the bone surface of the tibia and the bone surface of the femur, the ancillary device does not impose dislocation of the joint during its placement on the two bone surfaces, nor does it require sacrificing any of the ligaments of the joint. The ancillary device according to the present invention cooperates with the bone surfaces without entering the intra-articular cavity. This tailor-made ancillary device adapts to the morphology of the patient and permits implantation of a tailor-made prosthesis according to the pathology and/or dysfunction.

Advantageously, each ancillary part comprises, for the tibial surface and the femoral surface, a bearing surface intended to match at least partially a portion of the corresponding bone surface, said bearing surface delimiting a working zone on said bone surface, each part comprising at least two guide means, said at least two guide means defining distinct working axes for guiding the movement of at least one medical device along said working axes on the corresponding bone surface. This configuration thus makes it possible to avoid dislocation of the joint and to preserve the anatomy and the tissue and muscle structures of the patient.

In another embodiment, the guiding ancillary device is configured to cooperate with three bone surfaces.

Said guide means or at least one of said guide means is configured to define an abutment for the movement of said corresponding guiding device.

For example, in order to limit the displacement of the medical guiding device along the movement axis defined by said guide means—By way of example, the axial dimension $d1$ of the guide means limits the displacement of a tool of axial dimension $d2$ greater than $d1$ such that $d2-d1=$depth of penetration of the medical device in the damaged zone to be repaired.

The at least one guide means is chosen from among a tubular member, oriented slits, a displacement path, a hollow elongate member or combinations of these features.

Within the context of the present invention, a displacement path or guide path is understood as an object having a continuous or discontinuous surface in relief, for guiding the movement of at least one medical device to at least one working zone.

Purely by way of illustration, this object can have grooves opening out at each of their ends in order to allow at least one medical device to be guided through each of them. These grooves can have different shapes in order to guide said at least one corresponding medical device differently depending on the nature of the local modification to be made to the corresponding bone surface. An oriented slit is understood as a member having an opening to permit the passage of a medical device, so as to guide said medical device to the working zone on the surface of the bone end.

A tubular member is understood as a rectilinear member bored at its center with a likewise rectilinear lumen parallel to the main dimension of the tubular member.

In another embodiment, the guiding ancillary device comprises a plurality of guide means, said guide means being a combination of at least two guide means chosen from a tubular member, a guide path, an oriented slit.

A hollow elongate member is understood as a member having an internal channel or guide channel adapted to receive a medical device, the inner surface of said internal channel being a guide member for guiding and moving the tool toward the working zone at the bone end surface.

Each hollow elongate member has a channel for the passage of at least one medical device through said corresponding hollow elongate member, the inner wall of said hollow elongate member delimiting said channel defining a displacement surface of said medical device against at least part of which said medical device is intended to be moved in order to delimit the excursion of said medical device in said working zone of said corresponding bone surface.

Advantageously, the displacement surface of movement of the medical device is configured in such a way that the displacement of the tool on this surface determines the circumference of the local modification to be made to the bone surface.

The hollow elongate member comprises a free end, the inner wall of at least said free end is flared or oblong or has a flattened tubular shape, its cross section being elliptical or polygonal, for example rectangular or square.

The free end of the hollow elongate member is understood as the part nearest the bone surface.

By way of illustration, when the inner wall of said free end is oblong, the inner surface of said internal channel allows the medical device to be guided to the working zone at the surface of the bone end, and also the lateral displacement of the medical device on the working zone at the surface of the bone end.

The guide means and the shape of the internal channel will thus be determined according to the action to be performed in the working zone at the surface of the bone end.

According to this embodiment, the clear diameter of the internal channel will be determined depending on the action to be performed.

In another embodiment, when the ancillary device according to the present invention comprises at least two guide means including an internal channel, the guide means will be able to be identical or different, the diameter and/or the shape of the internal channel of each of the guide members will be able to be distinct, depending on the action to be performed.

In a preferred embodiment, all of the guide members are tubular members.

Each tubular member is a function of the corresponding bone surface of the patient to receive a medical device, of which at least the diameter is related to the dimensions of said bone surface.

The tubular member has a lumen defining a longitudinal axis for the displacement of at least one medical device along said axis.

The dimensions of the tubular member are such that said tubular member is adapted and intended to receive a medical device and to guide said medical device to the working zone at the surface of the bone surface, said medical device being inserted into the lumen of said tubular member.

In one embodiment, the tubular members are identical.

In another embodiment, the diameter of the lumen of the tubular members can be different depending on the medical device that is to be inserted into the lumen of said tubular member.

The guiding ancillary device comprises at least two guide means.

In a very particularly preferred embodiment, the guiding ancillary device comprises eight guide means, said eight guide means being tubular members.

The guide means define at least one working axis for guiding a medical device on said at least one working zone on the bone surface in order to locally modify at least a portion of said corresponding bone surface in said at least one working zone.

The tubular member comprises a main axis, this main axis is coincident with the working axis, the working axis of said guide member being directed along an axis tangent or substantially tangent at a point on the working zone.

The guide means is configured in such a way as to direct the medical device into a part of at least one of the working zones, said part being separate from a sensitive zone.

Within the context of the present invention, a sensitive zone is understood in particular as an innervated zone, a vascularized zone, a medullary zone. Thus, a sensitive zone is understood as the neurovascular bundle and the spinal cord, said sensitive zone being distinct from an osseous zone.

Advantageously, the ancillary device according to the present invention makes it possible to support the surgical procedure and guide it in order to avoid any of the sensitive zones.

The guiding ancillary device is made of a biocompatible hot-melt material.

Within the context of the present invention, a hot-melt material is understood as a material that becomes fluid under the effect of heat. Advantageously, the material of the ancillary device within the context of the present invention is biocompatible, that is to say it has the capacity not to interfere with and not to degrade the biological environment in which it is used. Examples that may be mentioned are metals and metal alloys such as stainless steels, particularly 316L stainless steel or 17-4PH stainless steel, titanium and titanium alloys such as titanium grade 1, grade 2, grade 4, grade 5, grade 23, ceramics such as alumina and zirconia, polymers such as copolymers of lactic acid and glycolic acid, polyanhydrides, polyamino acids, polyamides, materials of natural origin such as chitin, fucans, cellulose, coral and collagen.

Preferably, the material of the ancillary device is polyamide 12 or titanium.

Typically, the ancillary device according to the present invention will be able to be used throughout the surgical operation.

Purely by way of illustration, mention will be made of its use in osteosynthesis, arthrodesis, arthroplasty, vertebroplasty, osteotomy, neurosurgery and kyphoplasty.

Alternatively, the ancillary device according to the present invention will be able to be used as an ex vivo surgical training system (training model, training before surgery, validation of the operating method). It will also be able to be used on cadaver models with a view to obtaining proofs of concept.

Another aspect of the invention is a method for manufacturing a guiding ancillary device.

Thus, according to the invention, the method for manufacturing the guiding ancillary device comprises the following steps:

i. Acquisition of one or more images of at least two bone surfaces by computed tomography (CT scan, X-ray) and/or magnetic resonance imaging;

ii. 3D representation of the imaging of the at least two bone surfaces acquired in step i.;

iii. Determination of at least one working axis in order to locally modify at least one portion of at least one of said bone surfaces;

iv. Determination of at least one bearing surface on said bone surfaces for maintaining the ancillary device in position, at least one of said bearing surfaces delimiting at least one working zone in which it is sought to locally modify said at least one portion of at least one bone surface;

v. Positioning of at least one guide means, said at least one guide means being configured in such a way as to guide at least one medical device along said at least one working axis obtained in step iii;

vi. Determination of the shape and dimensions of the ancillary device from the working axes, of at least one bearing surface and of the at least one guide means;

vii. Realization of the ancillary device.

Very advantageously, the method according to the invention permits realization of an ancillary device, this ancillary device being a tailor-made ancillary device. The correct positioning of the ancillary device and its precision will depend on the quality of the images obtained. The image acquisition can be performed by computed tomography (CT) or magnetic resonance imaging (MRI) or by the combination of the CAD of computed tomography/magnetic resonance imaging.

Computed tomography has better spatial resolution, and the acquisition of images of the bone parts is more precise. In a preferred embodiment, magnetic resonance imaging would be used, since MRI permits precise visualization of the cartilage. In an even more preferred embodiment, the image acquisition is effected by the combination of the CAD of computed tomography/magnetic resonance imaging.

Said images thus acquired will then be segmented and modeled in 3D on a computer. Said images are transmitted by encoding. Purely by way of illustration, the format used is STL (surface tessellation language).

The 3D modeling of said at least two bone surfaces will make it possible to determine at least one bearing surface on said bone surfaces for maintaining the ancillary device in position, at least one of said bearing surfaces delimiting at least one working zone in which said at least one portion of at least one bone surface will be locally modified.

By virtue of the 3D modeling, it will then be possible to determine at least one working axis in order to locally modify at least one portion of at least one of said bone surfaces, and to position at least one guide means, said guide means being configured in such a way as to guide at least one medical device along said working axis.

Thus, the at least one guide means will advantageously be in the continuation of the working axis determined according to the surgical procedure, in order to guide the medical device to the working zone via the working axis.

The local modification of at least one of the bone ends may be chosen from osteosynthesis, arthrodesis, arthroplasty, vertebroplasty, osteotomy, neurosurgery and kyphoplasty.

Osteosynthesis is understood as all the methods for treating fractures or problems of a mechanical order. These include, for example, the placement of pins, screws, plates, rods and nails.

Arthrodesis is understood as an intervention intended to fix a joint by bone fusion and locked by osteosynthesis.

Arthroplasty is understood as a surgical intervention that involves restoring the mobility of a joint by creating a new articular space.

Vertebroplasty is understood as a surgical intervention that involves injecting cement into a pathological vertebral body.

Kyphoplasty is understood as a surgical intervention by which a balloon that can be inflated to several atmosphere is introduced transcutaneously into the fractured vertebral body.

Osteotomy is understood as a surgical procedure that involves cutting the diaphysis of a long bone for the purpose of better reorienting an axis or even several axes of said bone in order to better reposition the joints located above and below.

An example of arthroplasty is the production of a recess on at least one bone surface. In the context of production of a recess, the latter will be determined by a skilled person on the 3D representation of at least one of the bone surfaces. In one embodiment, the recess will be produced so as to be adapted and intended to receive an implant or prosthesis. In an even more preferred embodiment, the recess will be produced on at least two bone surfaces, so as to be adapted and intended to receive an implant or prosthesis.

In one embodiment, the implant or prosthesis has a shape chosen from among a U shape, a V shape or a W shape and will be an implant customized to the pathology and/or morphology of the patient.

Thus, the end of at least one of the bone surfaces will have to be modified locally so as to be adapted and intended to receive an implant or prosthesis, said implant or prosthesis having a shape chosen from among a U shape, a V shape or a W shape. Based on the shape of said implant or prosthesis identified and therefore on the projection of the local modification of the end of at least one of bone surfaces, the practitioner will be able to determine at least one working axis in such a way as to modify at least one portion of at least one of the bone ends.

Said guide means or at least one of said guide means being a hollow elongate member, each hollow elongate member having a channel delimited by an inner wall of said elongate member for the passage of at least one medical device through said corresponding hollow elongate member, in step v) at least the shape of said inner wall of each hollow elongate member is configured to delimit the excursion of said medical device into the corresponding working zone according to the local modification that is to be made in said corresponding bone surface.

The guide means and the shape of the internal channel will thus be determined according to the action to be performed in the working zone at the surface of the bone end.

In one embodiment, the inner wall of the free end, i.e. the end closest to the bone surface, of the hollow elongate member is flared or oblong or has a flattened tubular shape, with a cross section that is elliptical, polygonal, for example rectangular or square.

Thus, the displacement surface of the medical device is advantageously configured in such a way that the displacement of the tool on this surface determines the circumference of the local modification that is to be made to the bone surface.

The method for manufacturing the ancillary device moreover comprises an additional step of additive manufacturing of the at least two bone surfaces acquired in step ii.

Advantageously, the additive manufacturing of the at least two bone surfaces makes it possible to check the suitability of the guiding ancillary device, within the context of the present invention, with respect to the at least two bone surfaces.

The ancillary device is produced by additive manufacturing.

The additive manufacturing is chosen from the techniques of stereolithography, selective laser sintering (SLS), fused deposition modeling (FDM), selective laser melting (SLM), or any method of additive manufacturing such as electron beam melting (EBM).

The invention also relates to an ancillary device within the context of the present invention for its use in osteosynthesis, arthrodesis, arthroplasty, vertebroplasty, osteotomy, biopsy, neurosurgery and kyphoplasty.

The present invention also relates to a method for treating a subject requiring such treatment, said method comprising the use of an ancillary device within the context of the present invention for performing osteosynthesis, arthrodesis, arthroplasty, vertebroplasty, osteotomy, biopsy, neurosurgery and/or kyphoplasty.

The ancillary device is used to produce a recess on at least one bone surface.

In a preferred embodiment, the two bone surfaces correspond to the zone of juxtaposition defining a joint.

Purely by way of illustration, mention will be made of the intervertebral joints, the lumbosacral joint, the sacrococcygeal joint, the intercoccygeal joints, the sacroiliac joints, the symphysis pubis, the glenohumeral joint, the acromioclavicular joint, the humero-ulnar joint, the humeroradial joint, the proximal radio-ulnar joint, the radiocarpal joint, the distal radio-ulnar joint, the joints between the carpal bones, the carpometacarpal joints, the intermetacarpal joints, the metacarpophalangeal joints, the interphalangeal joints, the hip joint, the tibiofemoral joint, the patellofemoral joint, the proximal tibiofibular joint, the ankle joint, the distal tibiofibular joint, the joints between the tarsal bones, the tarsometatarsal joints, the intermetatarsal joints, the metatarsophalangeal joints, the interphalangeal joints.

In a preferred embodiment, the ancillary device is intended to cooperate with the tibiofemoral joint.

In another embodiment, the ancillary device is intended to cooperate with the hip joint.

In another embodiment, the joints concerned are those of the lumbar and cervical spine.

In another embodiment, the joint is the shoulder joint.

Finally, in another embodiment, the ancillary device is used to cooperate with at least one of the vertebrae of the cervical spine.

In an even more preferred embodiment, the guiding ancillary device is used in the production of a recess, preferably for the production of a recess adapted to receive an implant, said implant being a total knee prosthesis (TKP), more preferably a total knee prosthesis with customized resurfacing.

The invention also relates to an assembly comprising a guiding ancillary device within the context of the present invention and at least one medical device.

BRIEF DESCRIPTION OF THE DRAWINGS

Other advantages, aims and particular features of the present invention will become clear from the following description which is given for explanatory purposes and is not in any way limiting, and in which reference is made to the attached drawings in which.

DETAILED DESCRIPTION OF THE INVENTION

It will be noted first of all that the figures are not to scale.

First Embodiment: Ancillary Device for Placement of a Knee Resurfacing Implant

Figure 1:
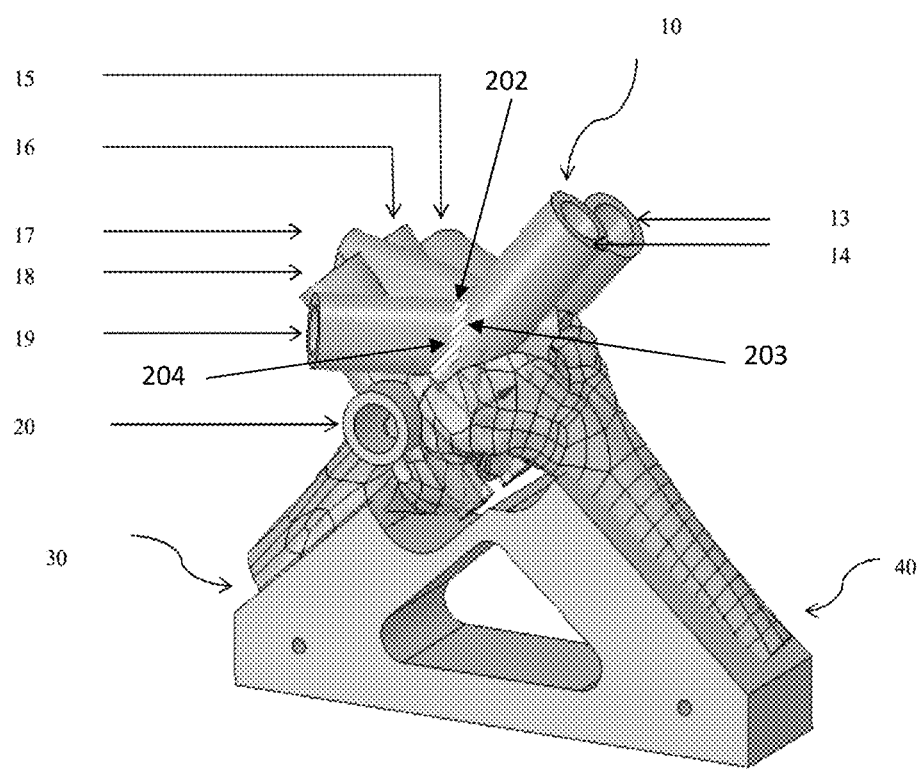
FIG. 1 is a perspective view of the proximal end of the tibia and the distal end of the femur, and also of the ancillary device according to a first embodiment, said ancillary device being in one piece and cooperating with said proximal end of the tibia and said distal end of the femur.

FIG. 1 is a perspective view of a guiding ancillary device 10 according to a first embodiment intended to cooperate with at least two bone surfaces, said two bone surfaces corresponding to the proximal end 30 of the tibia and the distal end 40 the femur.

The guiding ancillary device 10 comprises eight guide means, said guide means being tubular members 13, 14, 15, 16, 17, 18, 19, 20. The tubular members 13, 14, 15, 16, 17, 18, 19, 20 of the guiding ancillary device 10 are adapted to receive at least one medical device.

Advantageously, the guiding ancillary device, being in one piece according to this first embodiment, perfectly matches the proximal end of the tibia and the distal end of the femur and allows the guiding ancillary device 10 to be maintained in position. Even more advantageously, its preoperative positioning does not require dislocation of the tibiofemoral joint, nor sacrifice of ligaments. The one piece construction may be achieved by assembling two or more ancillary parts. For example, tubular members 14 and 19 may be provided as two ancillary parts that are joined together by a connection means 202, as shown in FIG. 1.

The guiding ancillary device 10 according to this first embodiment, and the eight tubular members 13, 14, 15, 16, 17, 18, 19, 20 of the guiding ancillary device 10, are made of biocompatible polyamide or titanium, depending on the required strength of the ancillary device.

Figure 2:
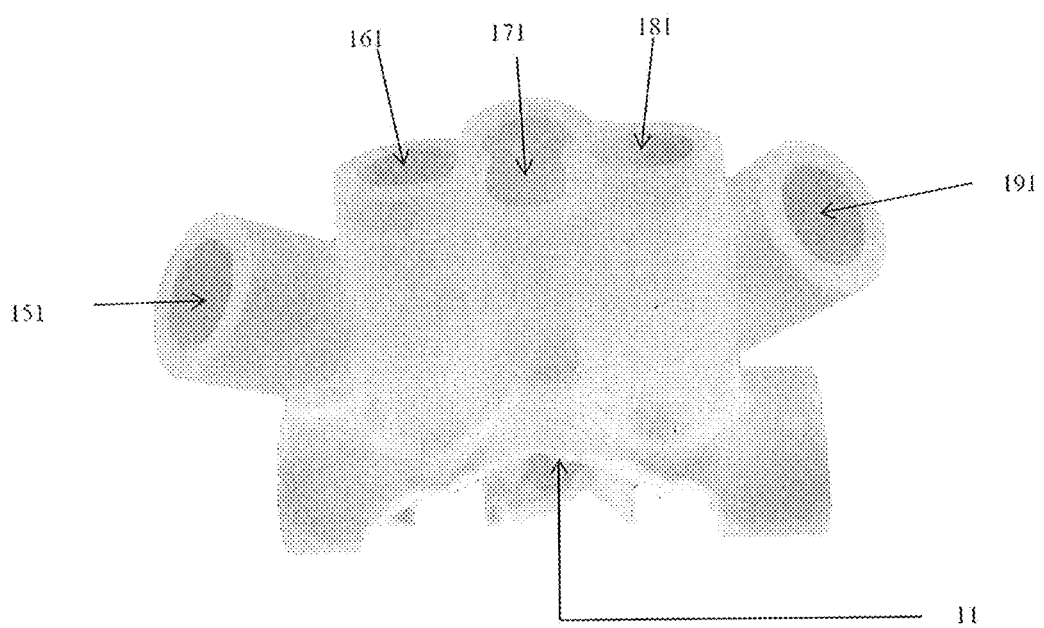
FIG. 2 is a photograph taken from the front and showing the tibial bearing surface.
Figure 3:
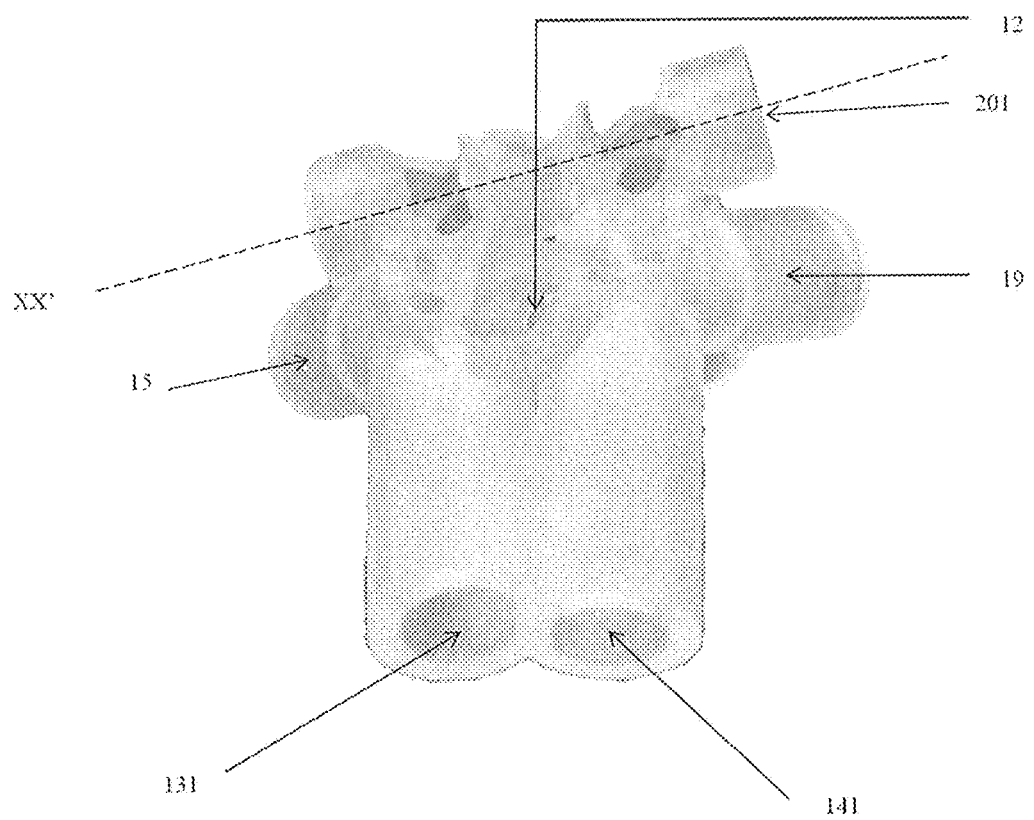
FIG. 3 is a photograph taken from below the ancillary device according to a first embodiment, showing the femoral bearing surface.

FIG. 2 is a photograph taken from the front and showing the tibial bearing surface. FIG. 3 is a photograph taken from below the ancillary device according to a first embodiment, showing the femoral bearing surface.

The members shown in FIG. 2 and bearing the same references as those of FIG. 1 represent the same items, which are not described again below.

The guiding ancillary device 10 comprises, for the proximal end of the tibia, a tibial bearing surface 11 intended to match part of the proximal end of the tibia, and, for the distal end of the femur, a femoral bearing surface 12 intended to match the distal end of the femur, said tibial bearing surface 11 and femoral bearing surface 12 advantageously allowing the ancillary device 10 to be maintained in position on the proximal end of the tibia and the distal end of the femur, respectively. The tibial bearing surface 11 and the femoral bearing surface 12 each delimit a working zone on the surface of each of the bone ends, namely the distal end of the femur for the femoral bearing surface 12 and the proximal end of the tibia for the tibial bearing surface 11.

Thus, according to this first embodiment, the guiding ancillary device 10 comprises eight tubular members 13, 14, 15, 16, 17, 18, 19, 20, each of the tubular members has a lumen 131, 141, 151, 161, 171, 181, 191, 201, and the lumen of each of the tubular members 13, 14, 15, 16, 17, 18, 19, 20 permits the rectilinear displacement of at least one medical device along a longitudinal axis.

According to this first embodiment, the guiding ancillary device 10 allows recesses to be formed at the end of the proximal tibial bone surface and at the end of the distal femoral bone surface.

According to this embodiment, the recesses at the end of the proximal tibial bone surface and at the end of the distal femoral bone surface are adapted and intended to receive a total knee prosthesis (TKP).

Thus, with the guiding ancillary device 10 according to the first embodiment comprising eight tubular members 13, 14, 15, 16, 17, 18, 19, 20, each of the tubular members corresponds to a working axis for guiding a medical device on each of the two working zones, respectively the tibial bearing surface 11 and the femoral bearing surface 12, in order to locally modify at least one portion of each of the bone ends in each of said working zones in order to form a recess.

Each of the working axes is coincident with the main axis of the lumen 131, 141, 151, 161, 171, 181, 191, 201 of each of the tubular members 13, 14, 15, 16, 17, 18, 19, 20 of the guiding ancillary device 10, the working axis of each of the tubular members 13, 14, 15, 16, 17, 18, 19, 20 being directed along an axis tangent or substantially tangent at a point on the distal femoral bone surface and the proximal tibial bone surface.

A working axis XX' is shown in FIG. 3.

According to this first embodiment, the guiding ancillary device is used to produce a recess, said recess being adapted and intended to receive a total knee prosthesis. Thus, the ancillary device according to this first embodiment is used to guide at least one medical device for producing at least one recess at the proximal tibial end and at least one recess at the distal femoral end.

Imaging is carried out by magnetic resonance imaging of the tibiofemoral joint, more precisely of the proximal tibial end and the distal femoral end.

The images of the bone surfaces thus acquired by magnetic resonance imaging will then be segmented and modeled in 3D on a computer, transmission of said images being in STL format. A 3D image of the tibiofemoral joint, i.e. of the proximal tibial end and the distal femoral end, is thus acquired.

On the basis of this 3D imaging of the tibiofemoral joint, the practitioner will determine the recesses required to receive a total knee prosthesis and thus to locally modify the distal femoral and proximal tibial bone ends.

Within the meaning of the present invention, a practitioner is understood as an engineer/prosthetist.

According to this embodiment, the total knee prosthesis corresponds to a U-shaped femoral implant and also to a U-shaped tibial implant.

The envisioned recess is the impression of each of the implants, such that the outer surface of each of the implants is flush or substantially flush with the bone surface of the tibial and femoral ends. The implant in this embodiment is a tailor-made implant adapted to the morphology/pathology of the patient.

From said recess projected onto the 3D image of the tibio-femoral joint, eight working axes will be determined for production of the recess on the surface respectively of distal femoral and proximal tibial bone ends. Two axes will be directed toward the femoral condyles, namely the medial condyle and the lateral condyle. One axis will be directed toward the patellar surface of the distal femoral end. Two axes will have for direction, and respectively, the zone of juxtaposition between the medial condyle of the distal end of the femur and the tibial plateau of the proximal end of the tibia and the zone of juxtaposition between the lateral condyle of the distal end of the femur and the lateral plateau of the proximal end of the tibia. Two axes will have for direction, and respectively, the medial tibial plateau and the lateral tibial plateau of the proximal end of the tibia. One axis will pass through the zone of juxtaposition of the medial tibial plateau and the medial femoral condyle and through the zone of juxtaposition between the lateral tibial plateau and the lateral femoral condyle. This axis is shown as axis XX' in FIG. 3.

From the working axes modifying the surface of the distal femoral end, the working surface of the distal femoral end will be determined, and, from the working axes modifying the proximal tibial end, the working surface of the proximal tibial end will be determined.

The working surface of the proximal tibial end and the working surface of the distal femoral end thus correspond respectively to the tibial bearing surface 11 and to the femoral bearing surface 12 of the guiding ancillary device 10.

The eight tubular members 13, 14, 15, 16, 17, 18, 19, 20 will be positioned in such a way that the longitudinal axis of the lumen 131, 141, 151, 161, 171, 181, 191, 201 of each of the tubular members coincides with the eight working axes determined by the practitioner.

FIG. 1 is a view of the right tibiofemoral joint of a patient, when the joint is at 90°.

The longitudinal axis of the lumen 131 of the tubular member 13 will thus correspond substantially to the working axis passing through the lateral condyle of the distal femoral end.

The longitudinal axis of the lumen 141 of the tubular member 14 of the ancillary device will correspond substantially to the working axis passing through the medial condyle of the distal femoral end.

The longitudinal axis of the lumen 171 of the tubular member 17 will correspond substantially to the working axis directed toward the patellar surface of the distal femoral end.

The longitudinal axis of the lumen 201 of the tubular member 20 will correspond to the working axis XX' directed and passing through the zone of juxtaposition of the medial tibial plateau and the medial femoral condyle and through the zone of juxtaposition between the lateral tibial plateau and the lateral femoral condyle, in order to produce a recess flush with the glenoid surface of the tibial plateau and the surface of the femoral condyle.

The longitudinal axis of the lumen 151 of the tubular member 15 will correspond substantially to the working axis directed toward the zone of juxtaposition between the lateral condyle of the distal end of the femur and the lateral plateau of the proximal end of the tibia, in order to produce a recess flush with the glenoid surface of the tibial plateau and the surface of the femoral condyle.

The longitudinal axis of lumen 191 of the tubular member 19 will correspond substantially to the working axis of the zone of juxtaposition between the medial condyle of the distal end of the femur and the tibial plateau of the proximal end of the tibia.

The longitudinal axis of the lumen 161 of the tubular member 16 will correspond substantially to the working axis directed toward the lateral tibial plateau of the proximal end of the tibia.

Finally, the longitudinal axis of the lumen 181 of the tubular member 18 will correspond substantially to the working axis directed toward the medial tibial plateau of the proximal end of the tibia.

The medical device according to the first embodiment is a milling device.

The eight tubular members 13, 14, 15, 16, 17, 18, 19, 20, each comprising a lumen 131, 141, 151, 161, 171, 181, 191, 201 having a longitudinal axis corresponding to each of the eight working axes previously determined at the surface of the bone surface, and the tibial bearing surface 11 and the femoral bearing surface 12 of the guiding ancillary device 10, corresponding to the working surfaces of the proximal tibial end and the distal femoral end will thus be determined in order to produce the guiding ancillary device 10 by 3D printing, according to the stereolithography technique if the ancillary device is to be made of titanium or stainless steel 316L, or by powder sintering if the ancillary device is to be made of polyamide 12.

Thus, the ancillary device according to this first embodiment is used in the production of a recess for the placement of a total knee prosthesis.

The guiding ancillary device 10 is thus intended to cooperate with the distal end 40 of the femur and the proximal end 30 of the tibia and comprises:

for the distal end 40 of the femur a femoral bearing surface 12 intended to match the distal end 40 of the femur, for the proximal end 30 of the tibia a tibial bearing surface 11 intended to match part of the proximal end 30 of the tibia, said bearing surfaces 11 and 12 each delimiting a working zone at the distal end of the femur for the femoral bearing surface 12 and at the proximal end of the tibia for the tibial bearing surface 11;

eight tubular members 13, 14, 15, 16, 17, 18, 19, 20 adapted to receive a milling device, said eight tubular members guiding the milling device to the two working zones, one at the distal end of the femur delimited by the femoral bearing surface 12, and one at the proximal end of the tibia for the tibial bearing surface 11.

The invention claimed is:

1. A guiding ancillary device intended to cooperate with two bone surfaces, said two bone surfaces corresponding respectively to the proximal end of the tibia and the distal end of the femur, characterized in that it comprises:

for each bone surface, a bearing surface intended to match at least partially a portion of the corresponding bone surface; said bearing surface delimiting a milling zone on said bone surface when it is in contact with said bone surface;

said bearing surfaces being configured to maintain said ancillary device in position on the corresponding bone surfaces, allowing the ancillary device to be maintained in position between the proximal end of the tibia and the distal end of the femur;

at least one guide means adapted to receive at least one milling device and one end of the at least one guide means directed toward the milling zone, said at least one guide means guiding the milling device to said milling zone on the corresponding bone surface to form a recess in the milling zone for the placement of an implant;

at least two ancillary parts, each of the ancillary parts being intended to cooperate with at least one distinct bone surface; and a first of said at least two ancillary parts having a female connection portion and a second of said at least two ancillary parts having a male connection portion, said first and second ancillary parts intended to be immediately contiguous when said ancillary device is assembled, said female connection portion and said male connection portion being intended to cooperate with each other in order to allow said ancillary parts to be joined together.

2. The guiding ancillary device as claimed in claim 1, characterized in that the guiding ancillary device is in one piece.

3. The guiding ancillary device as claimed in claim 1, characterized in that each bearing surface is an impression of the portion of the bone surface that it is intended to match.

4. The guiding ancillary device as claimed in claim 1, characterized in that it is configured to cooperate with two distinct bone surfaces.

5. The guiding ancillary device as claimed in claim 1, characterized in that said guide means or at least one of said guide means is configured to define an abutment for the movement of said corresponding guiding device.

6. The ancillary device as claimed in claim 1, characterized in that the at least one guide means is chosen from among a hollow elongate member, a tubular member, oriented slits, a displacement path, and combinations of these features.

7. The ancillary device as claimed in claim 1, characterized in that the at least one guide means is a tubular member, the tubular member has a lumen defining a longitudinal axis for the movement of at least one medical device along said axis.

8. The ancillary device as claimed in claim 1, characterized in that each guide means, or at least one of said guide means, comprises a hollow elongate member having a channel for the passage of at least one medical device through said corresponding hollow elongate member, the inner wall of said hollow elongate member delimiting said channel defining a displacement surface of said medical device against at least part of which said medical device is intended to be moved in order to delimit the excursion of said medical device in said working zone of said corresponding bone surface.

9. The ancillary device as claimed in claim 1, characterized in that the ancillary device comprises at least two guide means.

10. The ancillary device as claimed in claim 7, characterized in that the tubular member comprises a longitudinal axis, this longitudinal axis is coincident with a working axis, the working axis of said tubular member being directed along an axis tangent or substantially tangent at a point of the working zone.

11. The guiding ancillary device as claimed in claim 1, characterized in that it further comprises at least one fixing means for fixing said ancillary device to at least one bone surface.

12. The guiding ancillary device as claimed in claim 1, characterized in that at least one of the guide means is configured in such a way as to direct the medical device into a part of at least one of the working zones that is separated from a sensitive zone.

13. The guiding ancillary device as claimed in claim 1, characterized in that the ancillary device has at least two ancillary parts, each of the ancillary parts being intended to cooperate with at least one distinct bone surface.

14. The guiding ancillary device as claimed in claim 13, characterized in that the ancillary device comprises at least one connection means allowing said at least two ancillary parts to be joined together.

15. The guiding ancillary device as claimed in claim 13, characterized in that said ancillary parts are configured to define at least two axes for guiding one or more different medical devices when they are connected to each other.

16. The guiding ancillary device as claimed in claim 13, characterized in that each part of said ancillary device comprises, for each bone surface, a bearing surface intended to match at least partially a portion of said corresponding bone surface, said bearing surface adapted to delimit a working zone on said bone surface, each part comprising at least two guide means, said at least two guide means defining distinct working axes for guiding the movement of at least one medical device along said working axes on the corresponding bone surface.

* * * * *